United States Patent [19]

Magerlein et al.

[11] 4,360,683

[45] Nov. 23, 1982

[54] ANTIBIOTIC NODUSMICIN DERIVATIVES

[75] Inventors: Barney J. Magerlein; Howard A. Whaley, both of Portage, Mich.

[73] Assignee: The Upjohn Company, Kalamazoo, Mich.

[21] Appl. No.: 175,409

[22] Filed: Aug. 6, 1980

[51] Int. Cl.$^3$ ............................................ C07D 313/00
[52] U.S. Cl. ..................................... 549/266; 549/214;
549/60; 548/248; 548/236; 548/256; 548/127;
548/125; 548/463; 548/526; 548/374; 546/270;
546/256; 544/357; 544/405; 548/336; 548/206;
548/201; 424/279; 424/232; 424/250; 424/266;
424/270; 424/272; 424/273 R; 424/273 P;
424/274; 424/276; 542/403
[58] Field of Search ..................... 260/343.41; 542/403

[56] References Cited

U.S. PATENT DOCUMENTS 4,049,678  9/1977  Peterson ........................ 260/343.41
4,148,883  4/1979  Celmer et al. ...................... 424/122
4,251,511  2/1981  Whaley et al. ....................... 424/122

OTHER PUBLICATIONS

Corey et al. Jour. Amer. Chem. Soc. 94:17, 1972.
Celmer et al., Jour. American Chem. Soc. 102:12, Jun. 4, 1980.

Primary Examiner—Jane T. Fan
Attorney, Agent, or Firm—Roman Saliwanchik

[57] ABSTRACT

Novel antibacterially-active esters of antibiotic nodusmicin. Activity is demonstrated against *Staphylococcus aureus*, *Streptococcus pyogenes*, and *Sarcina lutea*. Thus, these esters can be used in various known environments, using well-known procedures, to eradicate or control susceptible microbes.

11 Claims, No Drawings

ANTIBIOTIC NODUSMICIN DERIVATIVES

DESCRIPTION

BACKGROUND OF THE INVENTION

Antibiotic nodusmicin (U-59,761) is producible in a fermentation under controlled conditions using a biologically pure culture of the microbe *Saccharopolyspora hirsuta* strain 367, NRRL 12045. This antibiotic is active against various bacteria, including *Mycobacterium avium, S. lutea, K. pneumoniae, B. fragilis,* and *C. perfringens*.

Our work to derive the structural formula for nodusmicin also enabled us to determine the structure for antibiotic U-59,760. We have determined that U-59,760 is the 9-O-pyrrole-2-carbonyl ester of nodusmicin.

The physical and chemical characteristics of U-59,760 cannot be distinguished from the antibiotic known as compound 47,444 which is disclosed in U.S. Pat. No. 4,148,883. Compound 47,444 is identified in U.S. Pat. No. 4,148,883 by its physical and chemical characteristics, as well as antimicrobial activity. The production of compound 47,444 in U.S. Pat. No. 4,148,883 is accomplished by an entirely different microbe, a Nocardia, than the *S. hirsuta* which produces nodusmicin. A recent publication in the Journal of the American Chemical Society discloses the structure of compound 47,444. See JACS, 102:12, June 4, 1980, pp. 4203–4209.

BRIEF SUMMARY OF THE INVENTION

Selective esterification of nodusmicin gives novel antibacterially active esters. Specifically, employing selective esterification procedures there are obtained 9-O-esters of nodusmicin which possess significant antibacterial activity. Other esters which are disclosed are the 18-O- and 11-O-esters which, though-possessing antibacterial activity, are much less active than the 9-O-esters. Also formed are di-O esters and tri-O esters. Antibiotic nodusmicin can be shown by formula I, infra.

In a broad aspect, the subject invention concerns esters formed by the reaction of nodusmicin with a hydrocarbon carboxylic acid of from 1 to 18 carbon atoms, inclusive; halo-, nitro-, hydroxy-, amino-, cyano-, thiocyano-, and loweralkoxy- substituted hydrocarbon carboxylic acid of from 1 to 18 carbon atoms, inclusive; and loweralkoxycarbonyl.

The most preferred esters of the subject invention are those wherein nodusmicin is reacted with acids of the generic structure A shown in Chart III.

Preferred esters of the subject invention are those wherein nodusmicin is reacted with acids of the generic structure B also shown in Chart III.

DETAILED DESCRIPTION OF THE INVENTION

We have determined that antibiotic nodusmicin (I) has three hydroxyl groups which we have labelled the C-18, C-9, and C-11 hydroxyls. Our work shows that the reactivity of the hydroxyls of nodusmicin to esterification and silylation decreases in the order $18>9>11$. Thus the hydroxyl at C-11 is much less reactive than the hydroxyl at C-18. Two processes can be employed to prepare esters of nodusmicin. One process is a random esterification of nodusmicin which produces mixtures containing some of the desired C-9 ester. This process is outlined in Chart I.

The preferred process, outlined in Chart II has three steps: (1) blocking of the most active C-18 hydroxy; (2) esterification of the C-9 hydroxyl; and (3) removal of the blocking group. These steps are now discussed in detail.

Step I. This step is the selective blocking of the most reactive C-18 hydroxyl. A suitable blocking group used in this sequence must have the following qualifications. It must react selectively in high yield with the C-18 hydroxyl. The resulting derivative must be stable during the esterification of the C-9 hydroxyl, be stable to chromatography, and easily cleaved leaving the C-9 ester intact.

A blocking group, as used herein, is one which will be removed prior to the obtention of the end product. It should be understood that at times an acyl group can function as a blocking group.

Exemplified herein is the use of the t-butyldimethyl silyl ether (BDM) at C-18. Other trisubstituted silyl ethers, for example, trimethylsilyl, triethylsilyl, methyl-di-isopropylsilyl or t-butyl-diphenylsilyl can be used. Other means to block the C-18 hydroxyl include substituted and unsubstituted tetrahydropyranyl ethers, $\beta,\beta,\beta$-trichloroethyl ether, $\beta$-methoxyethoxymethyl ether, carbonate esters, such as carbo-t-butoxy, carbobenzyloxy, substituted carbobenzoxyl and the like. When (1) is treated with t-butyldimethylsilyl chloride in an organic solvent in the presence of a base, such as imidazole [E. J. Corey and A. Venrateswarlu, *J. Amer. Chem. Soc.*, 94, 6190 (1972).], 18-O-ether (3) is formed in high yield. Isolation requires chromatography. In addition varying amounts of 9,18-O-diether (4) can be isolated.

Step 2. Esterification of silyl ether (3) usually gives preferentially C-9 ester (5) with varying amounts of C-11 ester (6) and diester (7). By limiting the amount of esterifying reagents employed, or length of reaction time, the formation of diester (7) can be suppressed, though sometimes this leads to lower yields of monoester and also greater amounts of unreacted ether (3). Two methods of esterification can be employed. Where acid chlorides are available, the acid chloride-pyridine esterification procedure is used. Generally, silyl ether (3) is treated with 1-3 molar equivalents of acid, 1.1-3.3 molar equivalents of dicyclohexylcarbodiimide and 0.1-0.3 moles of 4-dimethylaminopyridine [A. Hassner and V. Alexanian, *Tet. Letters*, 4475 (1978) and F. E. Ziegler and G. D. Berger, *Sym. Comm.*, 9, 539 (1979)]. The esterified products are usually isolated as a glass and characterized by cmr and high resolution ms. Mass spectral data for the esters are given in Table I. Table II gives chemical shifts for the C-13 NMR spectra for several typical BDM esters. Included are data for 9-O, 11-O and 9,11-di-O esters of 18-O-BDM-nodusmicin.

Step 3. Blocking groups are removed from the silyl ethers by treatment with fluoride ion (Bu$_4$NF) in tetrahydrofuran (THF) by the method of Corey (loc cit), or with dilute acid, to afford the appropriate ester. Purification is achieved by chromatography over silica gel.

In vitro antibacterial testing data, as measured by standard dipped disc agar diffusion assays and Minimum Inhibitory Concentration (MIC) determinations, are recorded in Table II.

The agar diffusion assay uses standard 12.7 mm paper discs. The disc is dipped in a 1 mg./ml. methanolic solution of the compound tested, dried, and applied to seeded agar trays. Inhibition zones are read after 16 hours of incubation.

MIC's are determined using the standard microplate broth-dilution method.

The broth used is BHI broth (Difco).

Compounds active against *S. aureus* can be used to disinfect washed and stacked food utensils contaminated with this bacterium. Further, the antibacterially-active esters of nodusmicin can be used as bacteriostatic rinses for laundered clothes, and for impregnating papers and fabrics; and, they are also useful for suppressing the growth of sensitive organisms in plate assays and microbiological media. These uses are well-known in the antibiotic art. Accordingly, bacteriological techniques are readily available to persons skilled in this art to practice such uses.

Acids which can be used in the esterification of nodusmicin are as disclosed above, and as shown in Chart III. In its broadest aspect, carboxylic acids suitable for esterification include (a) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic, octynoic acids, and the like; (b) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid, dipropylcyclohexanecarboxylic acid, and the like; (c) saturated or unsaturated, alicyclic aliphatic carboxylic acids, for example, cyclopentaneacetic acid, cyclopentanepropionic acid, cyclohexaneacetic acid, cyclohexanebutyric acid, methylcyclohexaneacetic acid, and the like; (d) aromatic carboxylic acids, for example, benzoic acid, toluic acid, naphthoic acid, ethylbenzoic acid, isobutylbenzoic acid, methylbutylbenzoic acid, and the like; and (e) aromatic-aliphatic carboxylic acids, for example, phenylacetic acid, phenylpropionic acid, phenylvaleric acid, cinnamic acid, phenylpropiolic acid and naphthylacetic acid, and the like. Suitable halo-, nitro-, hydroxy-, amino-, cyano-, thiocyano-, and lower alkoxyhydrocarbon carboxylic acids include hydrocarboncarboxylic acids as given above which are substituted by one or more of halogen, nitro, hydroxy, amino, cyano, or thiocyano, or loweralkoxy, advantageously loweralkoxy of not more than six carbon atoms, for example, methoxy, ethoxy, propoxy, butoxy, amyloxy, hexyloxy, and isomeric forms thereof. Examples of such substituted hydrocarbon carboxylic acids are:

mono-, di-, and trichloroacetic acid;
α- and β-chloropropionic acid;
α- and γ-bromobutyric acid;
α- and δ-iodovaleric acid;
mevalonic acid;
2- and 4-chlorocyclohexanecarboxylic acid;
shikimic acid;
2-nitro-1-methyl-cyclobutanecarboxylic acid;
1,2,3,4,5,6-hexachlorocyclohexanecarboxylic acid;
3-bromo-2-methylcyclohexanecarboxylic acid;
4- and 5-bromo-2-methylcyclohexanecarboxylic acid;
5- and 6-bromo-2-methylcyclohexanecarboxylic acid;
2,3-dibromo-2-methylcyclohexanecarboxylic acid;
2,5-dibromo-2-methylcyclohexanecarboxylic acid;
4,5-dibromo-2-methylcyclohexanecarboxylic acid;
5,6-dibromo-2-methylcyclohexanecarboxylic acid;
3-bromo-3-methylcyclohexanecarboxylic acid;
6-bromo-3-methylcyclohexanecarboxylic acid;
1,6-dibromo-3-methylcyclohexanecarboxylic acid;
2-bromo-4-methylcyclohexanecarboxylic acid;
1,2-dibromo-4-methylcyclohexanecarboxylic acid;
3-bromo-2,2,3-trimethylcyclopentanecarboxylic acid;
1-bromo-3,5-dimethylcyclohexanecarboxylic acid;
homogentisic acid, o-, m-, and p-chlorobenzoic acid;
anisic acid;
salicylic acid;
p-hydroxybenzoic acid;
β-resorcylic acid;
gallic acid;
veratric acid;
trimethoxybenzoic acid;
trimethoxycinnamic acid;
4,4'-dichlorobenzilic acid;
o-, m-, and p-nitrobenzoic acid;
cyanoacetic acid;
3,4- and 3,5-dinitrobenzoic acid;
2,4,6-trinitrobenzoic acid;
thiocyanoacetic acid;
cyanopropionic acid;
lactic acid;
ethoxyformic acid (ethyl hydrogen carbonate);
and the like.

Acids which can be used to make esters considered to be the most preferred are, for example, pyrrole-3-carboxylic,
4-bromo-2-pyrrolecarboxylic,
5-bromo-2-pyrrolecarboxylic,
4-nitropyrrole-2-carboxylic,
4-aminopyrrole-2-carboxylic,
4-methoxy-2-pyrrolecarboxylic,
4-hydroxy-2-pyrrolecarboxylic,
5-hydroxy-2-pyrrolecarboxylic,
4-methylpyrrole-2-carboxylic,
2-methylpyrrole-3-carboxylic,
thiophene-2-carboxylic,
thiophene-3-carboxylic,
3-chloro-thiophene-2-carboxylic,
5-nitro-thiophene-2-carboxylic,
amino thiophene-2-carboxylic,
3-methoxythiophene-2-carboxylic,
3-bromothiophene-2-carboxylic,
3-methylthiophene-2-carboxylic,
2-acetylaminothiophene-3-carboxylic,
3-methylthiophene-2-carboxylic,
2-methylthiophene-3-carboxylic,
4-bromomethylthiophene-3-carboxylic,
4-methoxymethylthiophene-3-carboxylic,
4-methylthioethylthiophene-3-carboxylic,
furoic,
3-furoic,
4-bromofuroic,
5-nitrofuroic,
5-aminofuroic,
4-methoxy-5-methyl-2-furoic,
4-hydroxyfuroic,
5-methylthiofuroic,
5-ethylfuroic,
and the like.

Acids which can be used to make esters considered to be preferred are, for example, imidazole-2-carboxylic,
4-imidazolecarboxylic,
5-methyl-2-imidazolecarboxylic,
4-(or 5)-amino-5-(or 4)-imidazolecarboxylic,
histidine, pyrazole-3-carboxylic,
pyrazole-4-carboxylic,
4-bromopyrazole-3-carboxylic,
3-methylpyrazole-5-carboxylic,
2-thiazolecarboxylic,
4-thiazolecarboxylic,
5-thiazolecarboxylic,
iso-oxazole-3-carboxylic,
isooxazole-5-carboxylic,
oxazole-4-carboxylic,
1,2,3-triazole-4-carboxylic,
and the like.

The above acids are well-known and available to those skilled in the art.

Preparation of Antibiotic nodusmicin

Part A. Fermentation

A biologically pure culture of Saccharopolyspora hirsuta strain 367, NRRL 12045, is used to inoculate 500-ml. Erlenmeyer seed flasks containing 100 ml. of sterile medium consisting of the following ingredients:

| Glucose monohydrate | 25 g./l. |
| Pharmamedia* | 25 g./l. |
| Tap water q.s. | 1 liter |

*Pharmamedia is an industrial grade of cottonseed flour produced by Traders Oil Mill Company, Fort Worth, Texas.

The seed medium presterilization pH is 7.2. The seed inoculum is grown for three days at 28° C. on a Gump rotary shaker operating at 250 rpm and having a 2½ inch stroke.

After three days incubation, the seed medium is used to inoculate (the inoculation rate is 5 ml. of seed inoculum per 100 ml. of fermentation medium) a series of 500-ml. Erlenmeyer flasks containing sterile fermentation medium consisting of the following ingredients:

| Glucose monohydrate | 10 g./l. |
| Dextrin | 20 g./l. |
| Corn steep liquor | 2.5 g./l. |
| $NH_4NO_3$ | 3.0 g./l. |
| NaCl | 2.0 g./l. |
| $CaCO_3$ | 5.0 g./l. |
| pH-7.2 (presterilization) | |

The fermentation flasks are incubated at a temperature of 28° C. on a Gump rotary shaker operating at 250 rpm and having a 2½ inch stroke. Harvest is usually after about 5 days of fermentation. A typical 5 day fermentation has the following titers of antibiotic in the fermentation broth:

| Day | S. lutea Assay, Bu/ml. |
|---|---|
| 2 | 8.0 |
| 3 | 10.4 |
| 4 | 10.4 |
| 5 | 11.2 |

In the assay results, a biounit (BU) is defined as the concentration of the antibiotic which gives a 20 mm. zone of inhibition under the standard assay condition. Thus, if, for example, a fermentation beer has to be diluted 1/100 to give a 20 mm. zone of inhibition, the potency of such beer is 100 Bu/ml.

B. Recovery and Purification

The whole beer (ca. 5,000 l.) from a fermentation, as described above, is adjusted to pH 7.3 with NaOH and filtered on a 30 inch filter press using diatomaceous earth as a filter aid. During the filtration operation wash water is applied to the filter cake. From the filtration operation is recovered 5,500 l. of clear fermentation broth which is then extracted twice with methylene dichloride (1,400 l. each time) to give a total of 2.800 l. of solvent extract. This solvent extract is concentrated in vacuo to 10 l. Assay on a standard S. lutea disc plate assay gives a value of 2,424 Bu/ml.

The extract concentrate described above (9 l.), is chromatographed over a column containing 9 kg. of silica gel (E. Merck-silica gel 7734). The column is eluted as follows:

20 liters methylene dichloride; then 40 liters 2% methanol in methylene dichloride; then 150 liters 5% methanol in methylene dichloride, then 100 liters 10% methanol in methylene dichloride. Four liter fractions are collected after an 80 liter forerun. Fractions 10–19 contain antibiotic nodusmicin. Crystalline antibiotic nodusmicin (41.4 g.) is obtained on concentration of fractions 10–19. Another 12.8 g. of crystalline antibiotic nodusmicin is obtained by chromatography of the mother liquors over silica gel with ethyl acetate as eluant.

The following examples are illustrative of the products and process of the invention, but are not to be construed as limiting. All percentages are by weight and all solvent mixture proportions are by volume unless otherwise noted.

EXAMPLE 1

Random Process of Ester Formation, Chart I 18-O- and 9-O-Benzoate Esters of nodusmicin.

Benzoyl chloride (560 mg., 4 mmoles) is added to 846 mg. (2 mmoles) of nodusmicin dissolved in 10 ml. of ethyl acetate and 480 mg. (6 mmoles) of pyridine. After standing at ambient temperature overnight, the reaction mixture is diluted with water and methylene dichloride. The methylene dichloride extract is washed successively with dilute acid and base. Following drying and evaporation, a mixture of crude benzoates is obtained. This material is chromatographed over 35 g. of Silica Gel 60 (EM Reagents) using Skellysolve B-ethyl acetate (4:1) for elution. Fractions are monitored by tlc (silica gel G; Skellysolve B-ethyl acetate) (4:1); and combined on the basis of the tlc profile. Fractions of 121 mg. (11.56% yield) of 18-O-benzoylnodusmicin and 92 mg. (8.7%) of 9-O-benzoyl-nodusmicin are obtained. Mol. wt. calculated for $C_{30}H_{38}O_8$: 526.2566. Found 18-O-benzoyl, 526.2591; 9-O-benzoyl, 526.2581. At a concentration of 1 mg./ml. a 0.5 inch disc gave a zone of inhibition on an agar tray seeded with S. lutea as follows: 18-O-benzoyl ester, 24 mm; 9-O-benzoyl ester, 30 mm.

EXAMPLE 2

Selective Process of Ester Formation, Chart II
Blocking of nodusmicin (Step 1)
18-O-t-Butyldimethylsilyl-nodusmicin (3) and
18,9-O-Di-t-butyldimethylsilyl-nodusmicin (4).

A solution of 2.16 g. (5.12 mmol) of nodusmicin, 1.7 g. (25 mmol) of imidazole and 1.5 g. (10 mmol) t-butyldimethylsilyl chloride in 25 ml. of dimethylformamide (DMF) is kept at ambient temperature for 18 hours. The solvent is distilled under vacuum. The residue is dissolved in methylene dichloride and washed several times with water. The solution is dried and concentrated. Chromatography over 105 g. of silica gel using chloroform-ethyl acetate (2:1) for elution affords 645 mg. (19.4%) of diether (4) and 1.787 g. (65.1%) of 18-O-ether (3).

Observed exact mass of molecular ion for (4) is 650.4034 (calculated for $C_{35}H_{62}O_7Si_2$, 650.4034); for (3) the observed is 536.3160 (calculated for $C_{29}H_{48}SiO_7$, 536.3169).

EXAMPLE 3

Esterification (Step 2) Acid-Carbodimide Procedure (Preferred Process) 9-O-Thiophene-3-carbonyl (5) and 9,11-O-Dithiophene-3-carbonyl-18-O-BDM-nodusmicin (7).

A mixture of 602 mg. (1.12 mmoles) of ether (3) from above, 272 mg. (2.13 mmoles) of thiophene-3-carboxylic acid, 482 mg. (2.3 mmoles) of dicyclohexylcarbodiimide, and 25 mg. of 4-dimethylaminopyridine in 20 ml. of THF is stirred at ambient temperature for 18 hours. The dicyclohexylurea which precipitates is removed by filtration and the filtrate evaporated. The residue is chromatographed over 35 g. of Silica Gel 60 using ethyl acetate-Skellysolve B (1:3) for elution. A fraction of 212 mg. (25.0% yield) of diester (7) is eluted first, followed by 357 mg. (49.3%) of 9-O-ester (5).

The exact masses of these products are as follows: 9-O-ester (5): calcd for $C_{34}H_{50}O_8SiS$ 646.2996; Found 646.2971. 9,11-O-Diester (7): calcd for $C_{39}H_{52}O_9SiS_2$ 756.2822; Found 756.2824.

EXAMPLE 4

Acid Chloride-Pyridine Procedure 9-O-2-Furoyl-11-O-2-Furoyl-, 9,11-O-Difuroyl-18-O-BDM-nodusmicin.

2-Furoyl chloride (2.02 mmoles, 270 mg.) is added to a cooled solution of 750 mg. (1.4 mmole) of ether (3) in 7 ml. of pyridine. After 30 minutes, 198 mg. additional furoyl chloride is added. The mixture is stirred for 30 minutes and diluted with methylene chloride. The resulting solution is washed successively with dilute acid and base. After drying and concentrating, the residue is chromatographed over 35 g. of silica gel. The column is eluted with Skellysolve B-ethyl acetate (4:1) to give: 9,11-O-diester, 129 mg. (14.1%); 9-O-ester, 325 mg. (40.9%) and 129 mg. of 11-O-ester (16.3%). The exact masses for these compounds are found in Table I.

EXAMPLE 5

Removal of Blocking Group (Step 3) 9-O-Thiophene-3-carbonyl-nodusmicin.

9-O-Thiophene-3-carbonyl-18-O-BDM-nodusmicin from above (357 mg.), is dissolved in 7.5 ml. of THF, and 2 ml. of tetrabutylammonium fluoride in THF (0.5 M) is added. After 30 minutes the mixture is evaporated. The residue is partitioned between water-ether. The ether solution is dried and concentrated. The residue is chromatographed over 25 g. of methanol (30:1). The product fraction weighs 247 mg. (84%) and is identified as 9-O-thiophene-3-carbonylnodusmicin. Exact mass; calcd for $C_{28}H_{36}O_8S$, 532.2131; Found 532.2127.

A solution of 1 mg./ml. when applied to a 0.5 inch disc and plated on agar trays seeded with the given organism, showed the following zones of inhibition: *S. lutea,* 40 mm.; *S. aureus,* 35 mm.

EXAMPLE 6

Upon reacting an appropriate acid having the acyl moiety shown in Table I with the 18-O-t-butyldimethylsilyl ether of antibiotic nodusmicin, there is obtained the corresponding ester.

EXAMPLE 7

Upon removal of the blocking group from the 18-position of the compounds in Example 6 with tetrabutylammonium fluoride, or a dilute mineral acid, for example, dilute HCl, there are obtained the compounds given in Table II.

Random Process of Ester Formation
Chart I

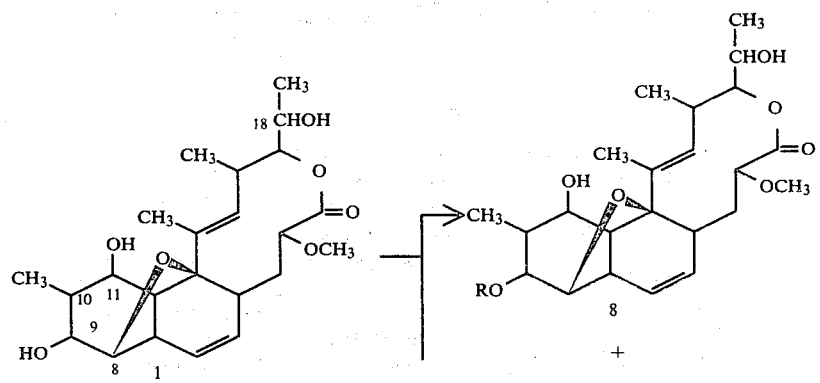

-continued
Random Process of Ester Formation
Chart I
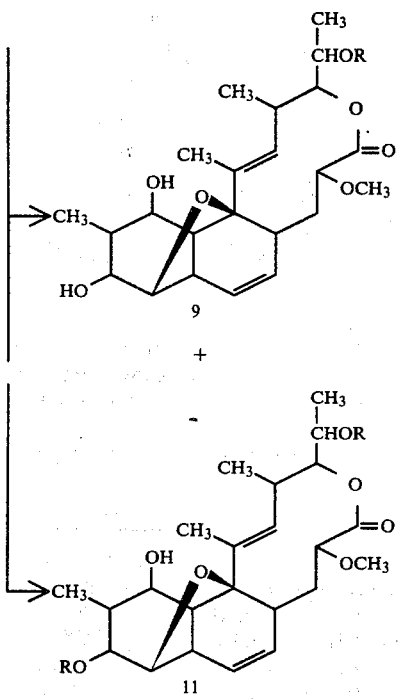
R = acyl
Selective Process of Ester Formation
Chart II
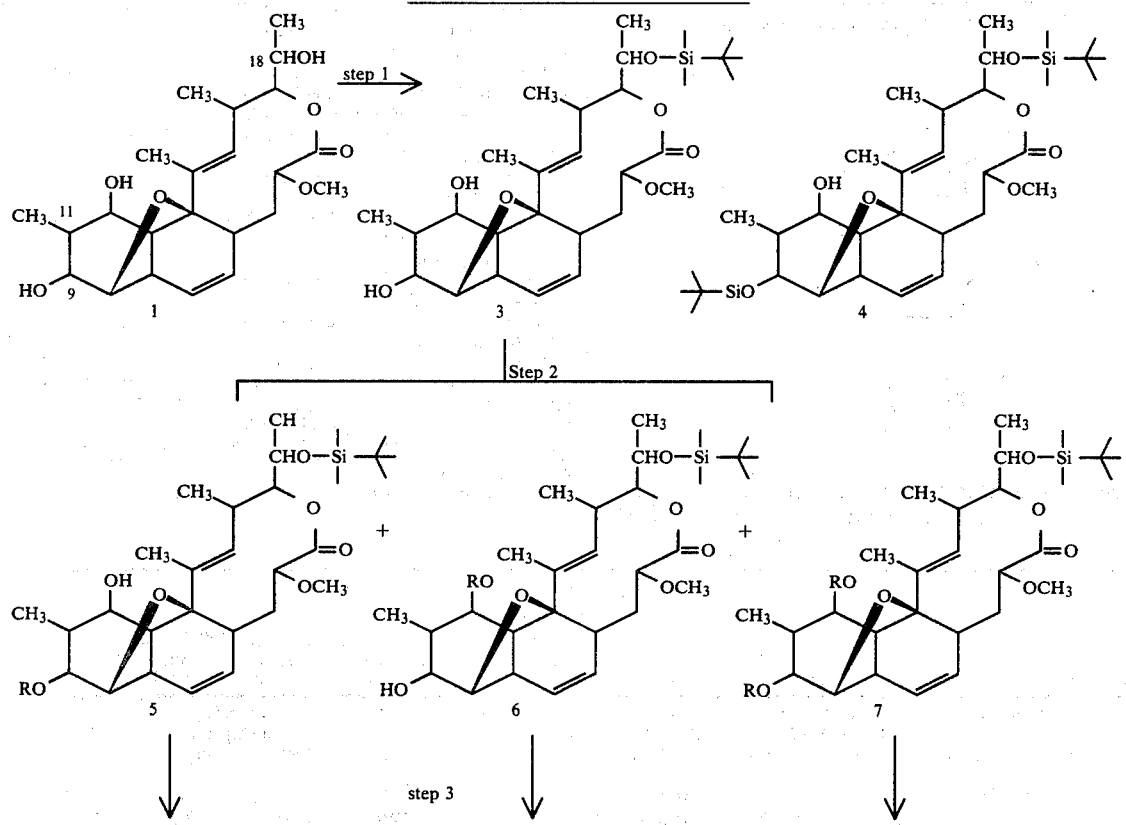

-continued
Selective Process of Ester Formation
Chart II

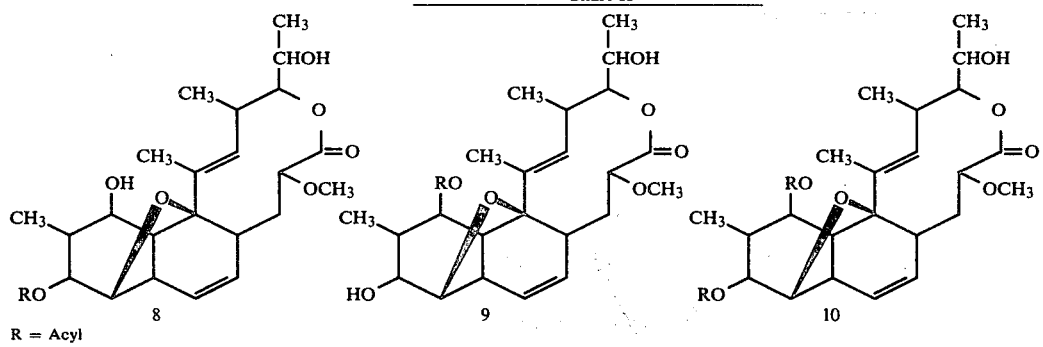

R = Acyl

Chart III

Most Preferred:

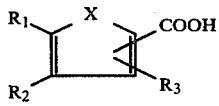

Structure A wherein X is selected from the group consisting of N, S, and O; $R_1$, $R_2$, and $R_3$ can be the same or different, and are selected from the group consisting of H, OH, halogen, $NO_2$, alkyl of 1-8 C, inclusive, $NH_2$, $NR_4 R_5$, wherein $R_4$ and $R_5$ can be selected from the group consisting of H, OH, and alkyl and substituted alkyl, wherein the alkyl is from 1 to 8 carbon atoms, inclusive, and the substituent on substituted alkyl can be OH, halogen, SH, and the like; O alkyl, S alkyl, O acyl, and N acyl; excluding wherein X is N, $R_1=R_2=R_3$ are H, and COOH is on the two position of the molecule.

Preferred:

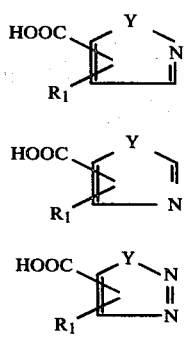

Structures B wherein Y is selected from the group consisting of nitrogen, sulfur or oxygen; COOH can be at any one of the unoccupied ring carbon atoms; and $R_1$ is as defined above and can be on any one of the unoccupied ring carbon atoms.

TABLE I
Esters of 18-O—BDM-Ether of nodusmicin

| Compound | Molecular Weight | | Exact Mass |
|---|---|---|---|
| 9-O—Benzoyl- | $C_{36}H_{52}O_3Si$ | 640.3431 | 640.3411 |
| 11-O—Benzoyl- | | | |
| 9,11-O—Dibenzoyl- | | | |
| 9-O—Nicotinoyl- | $C_{35}H_{51}O_8NSi$ | 641.3384 | 641.3394 |
| 9-O—2-Furoyl- | $C_{34}H_{50}O_9Si$ | 630.3224 | 630.3253 |
| 11-O—2-Furoyl- | | | 630.3209 |
| 9,11-O—Difuroyl- | $C_{39}H_{52}O_{11}Si$ | 724.3279 | 724.3251 |
| 9-O—N—Cbz-L-prolyl- | $C_{42}H_{61}O_{10}NSi$ | | |
| 9-O—N—t-BOC-L-prolyl- | | | |
| 9-O—Pyrrole-2-carbonyl- | $C_{34}H_{51}O_8NSi$ | 629.3384 | 629.3370 |
| 9-O—Picolinoyl- | $C_{35}H_{51}O_8NSi$ | 641.3384 | 641.3362 |
| 9-O—Thiophene-3-carbonyl- | $C_{34}H_{50}O_8SiS$ | 646.2996 | 646.2971 |
| 9,11-O—Dithiophene-3-carbonyl | $C_{39}H_{52}O_9SiS_2$ | 756.2822 | 756.2824 |
| 9-O—Isonicotinoyl- | $C_{35}H_{51}O_8NSi$ | 641.3384 | 641.3362 |
| 9,11-Di-O—isonicotinoyl- | $C_{41}H_{54}O_9N_2Si$ | 746.3598 | 746.3609 |
| 9-O—N—Methylpyrrole-2-carbonyl- | $C_{35}H_{53}O_8NSi$ | 643.3540 | 643.3510 |
| 9-O—5-Nitrofuroyl- | $C_{39}H_{51}O_{11}NSi$ | | |
| 9-O—Thiophene-2-carbonyl | $C_{34}H_{50}O_8SiS$ | 646.2996 | 646.3022 |
| 9-O—Pyrazine-2-carbonyl | $C_{34}H_{50}O_8N_2Si$ | 642.3336 | 642.3306 |
| 9,11-O—Dipyrazine-2-carbonyl | $C_{39}H_{52}O_9N_4Si$ | 748.3503 | 748.3527 |
| 9-O—5-Methylpyrrole-2-carbonyl | $C_{35}H_{53}O_8NSi$ | 643.3540 | 643.3555 |
| 9-O—Indole-2-carbonyl | | | |
| 9-O—5-Nitropyrrole-2-carbonyl- | $C_{34}H_{50}O_{10}N_2Si$ | 674.3234 | 674.3216 |
| 11-O—5-Nitropyrrole-2-carbonyl- | $C_{34}H_{50}O_{10}N_2Si$ | 674.3234 | 674.3234 |
| 9-O—4-Nitropyrrole-2-carbonyl | $C_{34}H_{50}O_{10}N_2Si$ | 674.3234 | 674.3209 |
| 9-O—3-Furoyl- | $C_{34}H_{50}O_9Si$ | 630.3224 | 630.3260 |
| 9,11-O—Di-3-furoyl- | $C_{39}H_{52}O_{11}Si$ | 724.3279 | 724.3236 |
| 9-O—5-Bromofuroyl- | $C_{34}H_{49}O_9BrSi$ | 708.2330 | 708.2349 |
| 9,11-O—Di-5-bromofuroyl- | $C_{39}H_{50}O_{11}Br_2Si$ | 880.1490 | 880.1503 |

Cbz = carbobenzoxy
t-BOC = tertiary butoxycarbonyl

TABLE II

| | | | | Esters of nodusmicin | | | | | |
|---|---|---|---|---|---|---|---|---|---|
| | | | | Agar Diffusion 1 mg./ml. | | MIC mcg./ml[3] | | | |
| U-No. | Name | Molecular Weight | Exact Mass | S. aureus UC 80 | S. lutea UC-130 | S. aureus UC-76[1] | S. aureus UC-570[1] | S. aureus UC-746[2] | S. pyrogenes UC-152 |
| | 18-O—benzoyl- | $C_{30}H_{38}O_8$ 526.2566 | 526.2591 | — | 24 | | insoluble | | |
| | 9-O—benzoyl- | $C_{30}H_{38}O_8$ 526.2566 | 526.2581 | — | 30 | | insoluble | | |
| 60,906 | 9-O—Nicotinoyl- | $C_{29}H_{37}O_8N$ 527.2519 | 527.2504 | NZ (no zone) | 32 | 250 | 250 | 250 | 2500 |
| 60,898 | 9-O—Furoyl- | $C_{28}H_{36}O_9$ 516.2359 | 516.2372 | 30 | 40 | 7.8 | 7.8 | 7.8 | >250 |
| 60,905 | 11-O—Furoyl- | $C_{28}H_{36}O_9$ 516.2359 | 516.2366 | NZ | 17 | 500 | 500 | 500 | >500 |

TABLE II-continued

Esters of nodusmicin

| U-No. | Name | Molecular Weight | Exact Mass | Agar Diffusion 1 mg./ml. S. aureus UC 80 | Agar Diffusion 1 mg./ml. S. lutea UC-130 | MIC mcg./ml[3] S. aureus UC-76[1] | MIC mcg./ml[3] S. aureus UC-570[1] | MIC mcg./ml[3] S. aureus UC-746[2] | MIC mcg./ml[3] S. pyrogenes UC-152 |
|---|---|---|---|---|---|---|---|---|---|
| 60,907 | 18-O—Pyrrole-2-carbonyl | $C_{28}H_{37}O_8N$ 515.2519 | 515.2508 | 27 | 33 | 7.8 | 3.9 | 15.6 | >250 |
| 60,908 | 9,18-O—Dipyrrole-2-carbonyl- | $C_{33}H_{40}O_9N_2$ 608.2734 | 608.2718 | 24 | 29 | insoluble | | | |
| 59,760 | 9-O—Pyrrole-2-carbonyl | — | — | 37 | 44 | 0.0625 | 0.0312 | 0.0312 | >125 |
| 60,909 | 9-O—Picolinoyl- | $C_{29}H_{37}O_8N$ 527.2519 | 527.2499 | NZ | 31 | >250 | >250 | >250 | >250 |
| — | 9,11-O—Dipicolinoyl- | $C_{35}H_{38}O_8N_2$ 614.2627 | 614.2605 | NZ | NZ | — | — | — | — |
| 60,910 | 9-O—Thiophene-3-carbonyl- | $C_{28}H_{36}O_8S$ 532.2131 | 532.2127 | 35 | 40 | 0.5 | 0.25 | 0.5 | 125 |
| 60,925 | 9-O—Isonicotinoyl- | $C_{29}H_{37}O_8N$ 527.2519 | 527.2509 | NZ | 38 | 250 | 250 | 250 | >250 |
| 60,933 | 9-O—L-Prolyl- | $C_{28}H_{41}O_8N$ 519.2832 | 519.2816 | 16 | 38 | 31.2 | 62.5 | 62.5 | >250 |
| 60,988 | 9-O—N—Methyl-pyrrole-2-carbonyl- | $C_{29}H_{39}O_8N$ 529.2675 | 529.2660 | NZ | 24 | 250 | >250 | 250 | 125 |
| 60,989 | 9-O—Thiophene-2-carbonyl- | $C_{28}H_{36}O_8S$ 532.2131 | 532.2105 | 27 | 41 | 3.9 | 3.9 | 3.9 | 125 |
| 60,990 | 9-O—5-Nitrofuroyl | $C_{28}H_{35}O_{11}N$ 561 | weak | NZ | 33 | 31.2 | 31.2 | 62.5 | 125 |
| 61,265 | 9-O—5-Methyl-pyrrole-2 carbonyl | $C_{29}H_{39}O_8N$ 529.2676 | 529.2665 | 20 | 30 | 31.2 | 31.2 | 31.2 | 125 |
| 61,264 | 9-O—Pyrrazine-2-carbonyl | $C_{28}H_{36}O_8N_2$ 528 | | NZ | 27 | >125 | >125 | >125 | >125 |
| 61,273 | 9-O—Indole-2-carbonyl- | $C_{32}H_{39}O_8N$ 565.2676 | 565.2690 | NZ | 22 | insoluble | | | |
| 61,427 | 9-O—5-Nitro-pyrrole-2-carbonyl- | $C_{28}H_{36}O_{10}N_2$ 560.2370 | 560.2414 | NZ | 32 | 125 | 250 | 125 | 250 |
| 61,462 | 9-O—4-Nitro-pyrrole-2-carbonyl- | $C_{28}H_{36}O_{10}N_2$ 560.2370 | 560.2387 | 20 | 36 | 15.6 | 31.2 | 31.2 | 125 |
| 61,461 | 9-O—3-Furoyl- | $C_{28}H_{30}O_9$ 516.2359 | 516.2376 | 35 | 41 | 0.50 | 0.25 | 0.50 | 2.50 |
| 61,463 | 9-O—5-Bromo-furoyl- | $C_{28}H_{35}O_9Br$ 594.1464 | 594.1492 | 0 | 35 | insoluble | | | |
| 59,761 | | | | NZ | 40 | 125 | 250 | 250 | 500 |
| 59,760 | | | | 38 | 44 | 0.125 | 0.175 | 0.125 | 62.5 |

[1]Sensitive strain
[2]Resistant to tetracycline
[3]Minimum Inhibitory Concentration

We claim:
1. A compound of the formula

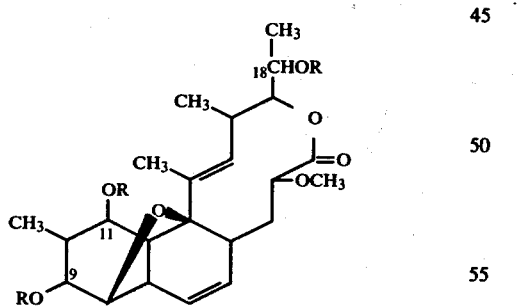

wherein R is H in no more than two positions at the same time, a blocking group which will be removed prior to the obtention of the end product, said blocking group selected from the group consisting of trisubstituted silyl ethers, tetrahydropyranyl ethers, $\beta,\beta,\beta$-trichloroethyl ether, and carbonate esters in at least one position, or an hydrocarbon carboxylic acid acyl of from 2 to 18 carbon atoms, inclusive; or a halo-, nitro-, hydroxy-, amino-, cyano-, thiocyano-, or loweralkoxy-substituted hydrocarbon acyl radical of from 2 to 18 carbon atoms, inclusive; and loweralkoxycarbonyl.

2. A compound of the formula, according to claim 1

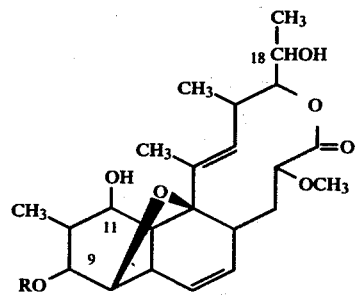

wherein R is an acyl radical containing from 2 to 18 carbon atoms, inclusive; or a halo-, nitro-, hydroxy-, amino-, cyano-, thiocyano-, or loweralkoxy-substituted hydrocarbon acyl radical of from 2 to 18 carbon atoms, inclusive; and loweralkoxycarbonyl.

3. A compound of the formula, according to claim 1

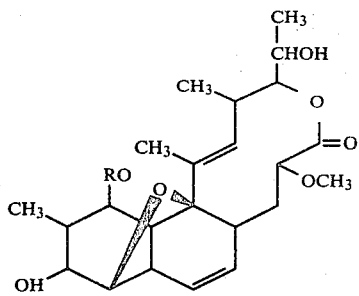

wherein R is an acyl radical containing from 2 to 18 carbon atoms, inclusive; or a halo-, nitro-, hydroxy-, amino-, cyano-, thiocyano-, or loweralkoxy-substituted hydrocarbon acyl radical of from 2 to 18 carbon atoms, inclusive; and loweralkoxycarbonyl.

4. A compound of the formula, according to claim 1

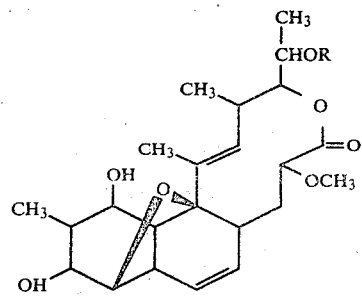

wherein R is an acyl radical containing from 2 to 18 carbon atoms, inclusive; or a halo-, nitro-, hydroxy-, amino-, cyano-, thiocyano-, or loweralkoxy-substituted hydrocarbon acyl radical of from 2 to 18 carbon atoms, inclusive; and loweralkoxycarbonyl.

5. 18-O-Benzoate ester of antibiotic nodusmicin.
6. 9-O-Benzoate ester of antibiotic nodusmicin.
7. 18-O-t-Butyldimethylsilyl ether of antibiotic nodusmicin.
8. 18,9-O-Di-t-butyldimethylsilyl ether of antibiotic nodusmicin.
9. 9-O-Benzoyl-18-O-butyldimethylsilyl ester of antibiotic nodusmicin.
10. 11-O-Benzoyl-18-O-butyldimethylsilyl ester of antibiotic nodusmicin.
11. 9,11-O-Dibenzoyl-18-O-butyldimethylsilyl ester of antibiotic nodusmicin.

* * * * *